United States Patent [19]

Boyles

[11] Patent Number: 5,167,628
[45] Date of Patent: Dec. 1, 1992

[54] AORTIC BALLOON CATHETER ASSEMBLY FOR INDIRECT INFUSION OF THE CORONARY ARTERIES

[76] Inventor: Paul W. Boyles, 1135 Kildaire Farm Rd., Cary, N.C. 27511-0640

[21] Appl. No.: 694,754
[22] Filed: May 2, 1991
[51] Int. Cl.⁵ .............................................. A61M 29/00
[52] U.S. Cl. ..................................... 604/101; 600/18; 604/53; 604/96
[58] Field of Search .................... 604/52-53, 604/96-99, 101-104; 606/191-192, 194; 600/18

[56] References Cited

U.S. PATENT DOCUMENTS

| | | | |
|---|---|---|---|
| 4,676,228 | 6/1987 | Krasner et al. | 128/4 |
| 4,753,221 | 6/1988 | Kensey et al. | 604/52 X |
| 4,795,427 | 1/1989 | Helzel | 604/53 |
| 4,824,436 | 4/1989 | Wolinsky | 604/53 |
| 4,909,252 | 3/1990 | Goldberger | 606/194 |
| 4,919,647 | 4/1990 | Nash | 600/16 |
| 5,078,685 | 1/1992 | Colliver | 604/96 |
| 5,108,370 | 4/1992 | Walinsky | 604/96 |

*Primary Examiner*—C. Fred Rosenbaum
*Assistant Examiner*—C. Maglione
*Attorney, Agent, or Firm*—Rhodes, Coats & Bennett

[57] ABSTRACT

A method and apparatus for indirectly infusing the coronary arteries involves insertion of a relatively large tubular member into the left ventricle to maintain blood flow from the left ventricle into the aorta. An isolated chamber within a segment of the aorta encompassing the opening to the coronary arteries is formed by inflating a pair of doughnut-shaped balloons attached at opposite ends of the tubular member. A catheter extends axially through the tubular member and includes a passage for infusing a treatment material into the isolated chamber. The treatment material is subsequently drawn into the coronary arteries which form the only exit from the isolated chamber.

7 Claims, 1 Drawing Sheet

AORTIC BALLOON CATHETER ASSEMBLY FOR INDIRECT INFUSION OF THE CORONARY ARTERIES

FIELD OF THE INVENTION

The present invention relates to a method and apparatus for selective indirect infusion of the coronary arteries without catheterization of the coronary arteries.

BACKGROUND OF THE INVENTION

A coronary thrombosis occurs when the coronary arteries, which originate at the root of the aorta and supply blood to the heart, become occluded by a blood clot. A coronary thrombosis may result in the destruction or severe deterioration in the condition of the heart muscle and may ultimately lead to death.

One method of treating a coronary thrombosis is to inject a fibrin clot-dissolving enzyme intravenously into the patient. The enzyme attacks and dissolves the blood clot to reopen the occluded artery. Relatively large doses of the enzyme are generally required when injected intravenously due to dilution or inactivation of enzyme by the active agent in the circulating blood. One risk inherent in this procedure is the destruction of the procoagulant and the anti-coagulant blood factors which produces a dangerous re-thrombosis and hemorrhage, such as a Hemorrhagic Stroke, resulting in brain damage and/or death.

Direct catheterization of the coronary arteries is another method used to infuse the coronary arteries with an enzyme during coronary thrombosis. Direct catheterization of the coronary arteries, however, may traumatize or damage the inner lining of the arteries. Further, direct catheterization requires highly skilled doctors with special training. Doctors capable of performing a direct catheterization are not available in many hospitals.

Use of balloon-type catheter to infuse medication into the arteries is known. For example, my own U.S. Pat. No. 4,705,502 describes a catheter with two round balloons to isolate an arterial segment to selectively profuse the artery. However, pressure on the upstream side of the catheter builds up quickly and tends to push the catheter out of the desired position.

Based on the forgoing, is clear that a new technique is needed to allow for profusion of the coronary arteries during a coronary thrombosis. Such a new technique should avoid direct catheterization of the coronary arteries.

SUMMARY OF THE INVENTION

The present invention involves the selective indirect infusion of the coronary arteries by isolating the aorta segment in close proximity to the openings to the coronary arteries. The isolated segment of the aorta is profused with a fibrin clot-dissolving enzymes, radio-opaque dye or drug therapy. Once the material has been introduced into the isolated area, it is quickly drawn into the coronary arteries which provide the only outlet to the isolated area.

The isolation of the aorta is accomplished by means of a double balloon arterial catheter. The catheter includes a thin-walled rubber tube attached at both ends to a donut-shaped ballon. The distal balloon is inserted into the left ventricle of the heart through the semilunar valve. The proximal balloon is spaced downstream of the opening to the coronary arteries. Upon inflation of the balloons, the entire root of the aorta is isolated while continued flow of blood through the thin-walled rubber tube is permitted. The flow of arterial blood from the left ventricle will push the distal balloon against the lower surface of the semilunar valve stabilizing the catheter in the desired position. The rubber tubing allows the passage of the main volume of blood with each heartbeat while the proximal balloon prevents the leak of blood back toward the heart. This combination provides an isolated aorta segment without any significant obstruction to the flow of blood thereby preventing pressure buildup which might tend to displace the catheter.

Selective indirect infusion of the coronary arteries also permits the enzyme, dye or drugs to reach the arteries quickly with a high concentration since there is no dilution or inactivation by the active agent in the circulating blood. There is remarkably improved response to treatment and increased effectiveness of the enzymes by ten-fold. Since less enzymes are needed, there is less destruction of the procoagulant and the anti-coagulant blood factors than with intravenous dosages. Therefore, the method of the present invention is far safer from adverse effects because of the lower dosage needed to accomplish complete clot lysis.

Accordingly, it is an object of the present invention to provide a new method an apparatus for infusion the coronary arteries with clot-dissolving enzymes, radio-opaque dyes, or drugs.

Another object of the present invention is to provide a new method and apparatus for infusing the coronary arteries without direct catheterization of the coronary arteries.

Another object of the present invention is to provide a double balloon-type catheter for isolating a segment of the aorta which will be more stable than prior art catheters and which will remain in the desired position for longer periods of time.

Another object of the present invention is to provide a double balloon-type catheter which will permit continued flow of the main volume of blood with each heart beat thereby minimizing the build-up of pressure which tends to displace the catheter.

Other objects and advantages of the present invention will become apparent and obvious from a study of the following description and the accompanying drawings which are merely illustrative of such invention.

DESCRIPTION OF THE INVENTION

Figure 1:
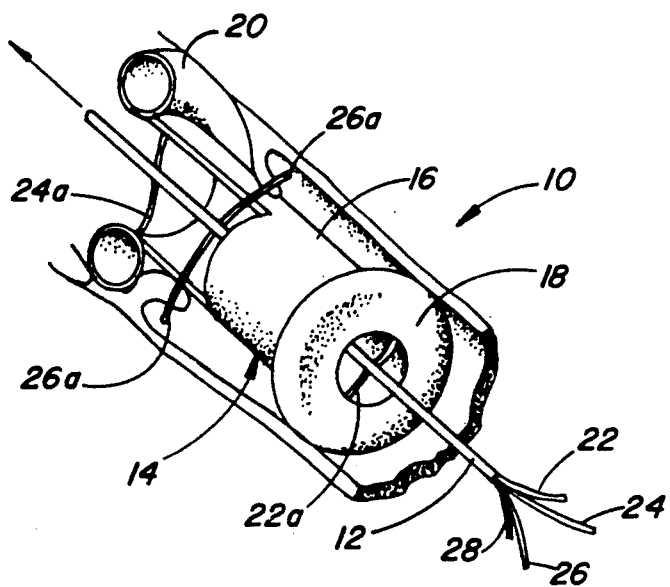
FIG. 1 is a perspective view of the aortic double balloon catheter assembly of the present invention.

Referring now to the drawings, and particularly to FIG. 1, an aortic balloon assembly catheter particularly designed for use in connection with the present invention is shown therein and indicated generally by the numeral 10. The aortic balloon catheter assembly includes a four lumen catheter 12 having a double balloon cannula 14 secured at the distal end of the catheter 12.

The cannula 14 includes a thin-walled rubber tube 16 having doughnut-shaped balloons 18 and 20 disposed at opposite ends thereof. The catheter 12 passes axially through the cannula 14 and terminates just beyond the distal balloon 20.

The catheter 12 has four lumens 22, 24, 26, and 28. Lumen 22 communicates with the interior of the proximal balloon 18 through the lumen branches 22a. Thus, balloon 18 can be inflated and deflated by applying positive and negative pressures through lumen 22. A second lumen 24 is used to inflate the distal balloon 20. The second lumen 24 communicates with the interior of balloon 20 through the lumen branches 24a. A third lumen 26 is used to communicate with the isolated area between the balloons 18 and 20 through lumen branches 26a. Lumen 26 is used to infuse clot-dissolving enzymes, radio-opaque dyes, or drugs into the isolated area. The fourth lumen 28 opens to the end of the catheter 12 and is used to infuse medication or other material directly into the left ventricle of the heart.

Figure 2:
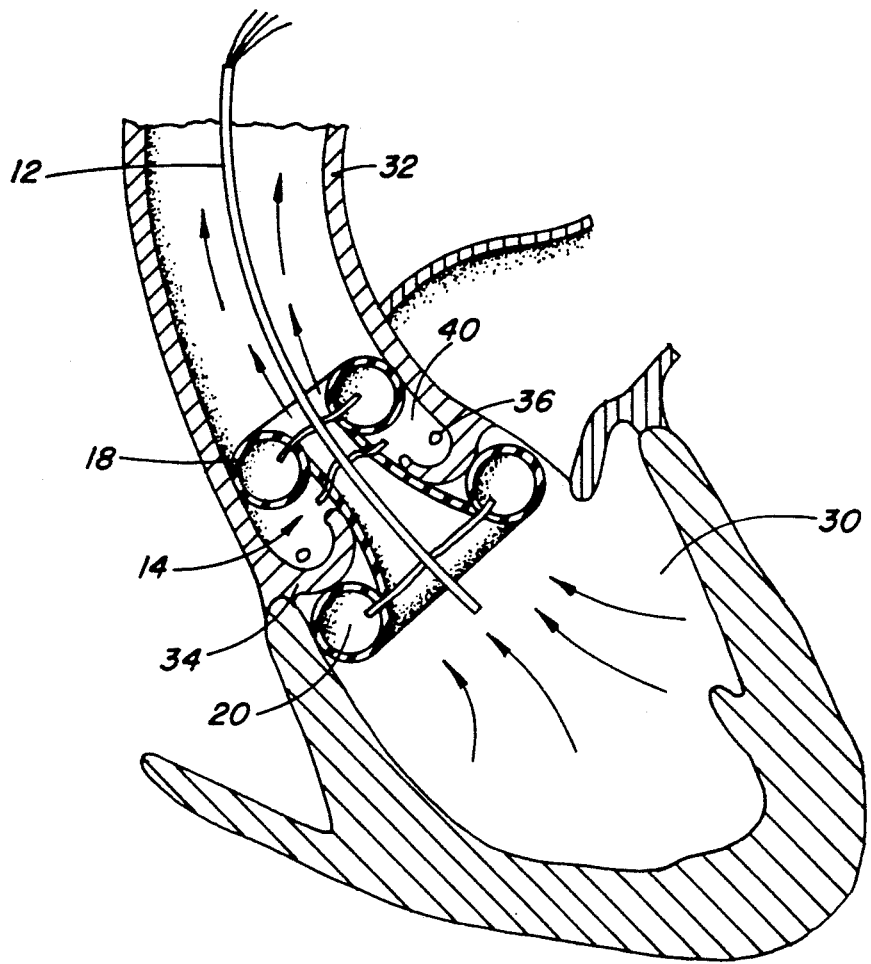
FIG. 2 is a section view of the catheter inserted into the left ventricle and aorta.

Referring now to FIG. 2, the aortic balloon catheter assembly 10 is shown being inserted into a patient's heart. The heart is shown as containing a left ventricle 30. The aorta 32 commences in the upper portion of the left ventricle 30 and conveys the oxygenated blood to the tissues of the body. The aortic opening is guarded by the semilunar valves 34 which surrounds the opening to the aorta. In the root of the aorta 32, there are two openings 36 leading to the coronary arteries which supply blood to the heart muscle. A coronary thrombosis occurs when these coronary arteries 36 become occluded by blood clots.

The aortic balloon catheter assembly 10 of the present invention is particularly designed to allow infusion of the coronary arteries without direct catheterization of the arteries. More particularly, the aortic balloon catheter assembly is inserted into the aorta 32 until the distal balloon 20 is pushed pass the semilunar valve 34. The proximal balloon 18 is then inflated by supplying pressure through lumen 22. Upon inflation, balloon 18 will press against the interior walls of the aorta 32 to stabilize the catheter 10. Next, the distal balloon 20 is inflated so that it engages the interior walls of the left ventricle 30. Upon inflation of the distal balloon 20, the flow of blood from the left ventricle will push balloon 20 up against the lower surface of the semilunar valves 34. The rubber tube 16 allows the passage of the main volume of blood with each heart beat while the proximal balloon 18 prevents the leak of blood back toward the heart. The rubber tubing 16 of the cannula 14 should be sufficiently flexible so that the semilunar valve 34 can close during diastole and collapse the tube 16 to prevent the back flow of blood into the left ventricle. Also, the rubber tubing 16 should be sufficiently strong to withstand pressures of up to 200 lbs/in².

The combination of the thin-walled rubber tube 16 with the two doughnut-shaped balloons 18 and 20 provides an isolated aorta segment without any significant obstruction to the flow of blood with each heartbeat. Thus, there will not be any significant build-up of pressure on the upstream side of the catheter as with prior art devices, thus allowing the catheter to remain in a fixed position for long periods of time.

It will also be noted that when balloons 18 and 20 are inflated, a segment of the aorta in the proximity of the openings to the coronary arteries is isolated. This isolated area is indicated by the numeral 40. Thus, the coronary arteries provide the only substantial exit from this isolated area 40. Fibrin clot-dissolving enzymes, radio opaque dye or drug therapy can be infused into the isolated area 40 through lumen of catheter 12. Substantially all of the material infused into the isolated area 40 must exit through the coronary arteries 36. This simple method of profusing the coronary arteries avoids the trauma, or damage to the inner lining of the arteries which sometimes occurs with direct catheterization of the arteries. Further, the selective indirect infusion of the coronary arteries permits the enzyme, dye or drugs to reach the arteries quickly with a high concentration since there is no dilution or inactivation by the active agent in the circulating blood. Accordingly, there is a much improved response to treatment and increased effectiveness of the enzyme by ten-fold. Because less enzyme is needed, there is less destruction of the procoagulant and anticoagulant blood factors than with the current intravenous dosage. Since a lower dosage is needed to accomplish to complete clot lysis, the method of the present invention is far safer than intravenous injection.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. An aortic balloon catheter assembly for indirect infusion of the coronary arteries comprising:
   (a) an elongated, flexible catheter having a relatively small diameter adopted for insertion into the aorta;
   (b) a canula secured to the distal end of the catheter, said cannula including:
      (1) a thin-walled, flexible tubular member having a relatively large diameter surrounding the distal end of the catheter; and
      (2) first and second balloons attached at opposite ends of the tubular member;
   (c) inflation means communicatively connected with the first and second balloons for inflating the first and second balloons after insertion of the catheter into the aorta so as to isolate a segment of the aorta while allowing blood to continue flowing to the large tubular member;
   (d) inflation means extending through said catheter for infusing a treatment material into the isolated area of the aorta between the first and second balloons; and
   (e) a lumen extending through the flexible catheter and communicating with an area upstream from the isolated area for infusing treatment material beyond the isolated area.

2. The aortic balloon catheter assembly of claim 1 wherein said catheter includes two inflation lumens for communicating with the first and second balloons.

3. The aortic balloon catheter assembly according to claim 1 wherein the tubular member is expandable and collapsible.

4. An aortic catheter assembly for delivering enzymes, radio-opaque dyes or drugs to the coronary arteries, said catheter assembly comprising:
   (a) an elongated, flexible catheter having a relatively small diameter;
   (b) a cannula disposed about the distal end of said catheter and adapted to be inserted into the left ventricle of the heart, said cannula including:
      (1) a thin-walled tubular member having a relatively large diameter surrounding the distal end of the catheter, wherein said tubular member is adapted to pass through the semilunar valve to enable blood to flow from the left ventricle into the aorta, and wherein the walls of the tubular member are sufficiently pliable to permit collapsing of the tubular member by the semilunar valve during diastole whereby backflow of blood into the left ventricle is prevented; and (2) first and second balloons for anchoring the catheter and isolating a segment of the aorta adjacent the coronary arteries, wherein said first balloon is secured to the distal end of the tubular member and is adapted to inflate against the interior surfaces of the left ventricle, and wherein the second balloon is secured to the proximal end of the tubular member and is adapted to be inflated against the inner surface of the aorta;

(c) inflation means communicatively connected to said first and second balloons for inflating the first and second balloons to form an isolated chamber surrounding said tubular member and between said balloons, wherein the coronary arteries form the only exit from said isolated chamber; and (d) a passage extending through said catheter and communicating with the isolated chamber for infusing material into the isolated chamber.

5. A method for infusing clot-dissolving enzymes, radio-opaque dyes, or drugs into the coronary arteries of a patient, said method comprising:

(a) inserting a tubular member through the aorta into the left ventricle of the patient's heart such that the tubular member defines a blood flow passage communicating with the left ventricle and the aorta;

(b) forming an isolated chamber within a portion of the aorta in which the openings to the coronary arteries are present such that said openings constitute the only substantial exit from the isolated chamber and wherein such chamber forms an annulus surrounding the tubular member;

(c) infusing the treatment material into said isolated chamber so that the material will be subsequently drawn into the coronary arteries.

6. The method according to claim 5 wherein the isolated chamber is formed by inflating a pair of doughnut-shaped balloons disposed at opposite ends of said tubular member such that said balloons form a seal surrounding said tubular member.

7. A method for infusing clot-dissolving enzymes, radio-opaque dyes, or drugs into the coronary arteries of a patient comprising the steps of:

(a) isolating a segment of the aorta such that the openings to the coronary arteries form the only exit from the isolated area;

(b) providing a blood flow passage communicating with the left ventricle of the heart and the aorta at a point downstream from the isolated area, so that blood flow from the heart is not interrupted; and (c) infusing a treatment material into the isolated area of the aorta so that the material will be subsequently drawn into the coronary arteries.

* * * * *